United States Patent [19]

Verduijn

[11] Patent Number: 4,994,249
[45] Date of Patent: Feb. 19, 1991

[54] ZEOLITE ZK-5

[75] Inventor: Johannes P. Verduijn, Spijkenisse, Netherlands

[73] Assignee: Exxon Chemical Patents Inc., Linden, N.J.

[21] Appl. No.: 183,801

[22] Filed: Apr. 20, 1988

[30] Foreign Application Priority Data

Apr. 22, 1987 [GB] United Kingdom ................. 8709507

[51] Int. Cl.$^5$ .............................................. C01B 33/28
[52] U.S. Cl. .................................... 423/328; 423/329
[58] Field of Search ............... 423/326, 328, 329, 331, 423/332; 502/85, 86

[56] References Cited

U.S. PATENT DOCUMENTS

| | | | |
|---|---|---|---|
| 3,247,195 | 4/1966 | Kerr | 428/328 |
| 3,720,753 | 3/1973 | Robson | 423/329 |
| 4,001,106 | 1/1977 | Plank et al. | 208/75 |
| 4,496,528 | 1/1985 | Bourgogne et al. | 423/328 |
| 4,503,023 | 3/1985 | Breck et al. | 423/328 |

OTHER PUBLICATIONS

Kerr, G. T. "Chemistry of Crystalline Aluminosilicates III, The Synthesis and Properties of ZK-5", Inorganic Chemistry vol. #5, No. 9, Sep. 1966, pp. 1539-1541.
Breck, D. W. "Zeolite Molecular Sieves", Wiley and Sons, 1974, pp. 111-113, 180, 309-310, 370.
Barrer, R. M. "Hydrothermal Chemistry of Zeolites", Academic Press 1982 pp. 17, 158-160, 210-212, 203,319-322, 334-335.

Primary Examiner—John Doll
Assistant Examiner—R. Bruce Breneman
Attorney, Agent, or Firm—E. F. Sherer

[57] ABSTRACT

Zeolites having the ZK-5 structure but having a silica/alumina ratio of up to 10 may be prepared by the use of strontium in the synthesis gel, and such zeolites may be useful in hydrocracking, reforming and separation.

4 Claims, No Drawings

ZEOLITE ZK-5

This invention relates to zeolite ZK-5, its preparation and use in catalysis. In particular, it relates to zeolite ZK-5 containing and/or synthesized using, strontium.

Zeolite ZK-5 has been known for some time as a catalyst for cracking hydrocarbons as described in "Zeolite Molecular Sieves", D. W. Breck, pages 111-113, 180 it is described as an aluminosilicate of the formula:

$$(R_1Na_2)O/Al_2O_3/4.0-6.0 SiO_2/6H_2O$$

(where R is derived from 1,4-dimethyl-1,4-diazocyclo [2,2,2,] octane). U.S. Pat. Nos. 3,247,195 and 4,001,106 describe ZK-5 as having a composition in terms of mole ratio of oxides as:

$$0.3-0.7R_{2/m}O:0.3-0.7M_{2/n}O:1Al_2O_3:4.0-6.0SiO_2:6-10H_2O$$

where R is as defined above or a mixture with hydrogen and m is the valence of R' and M is a metal of valence n. In U.S. Pat. No. 3,247,195 ZK-5 is reported as having an X-ray diffraction pattern with the following d(A) values and intensities:

| d(A) | Relative Intensity (I/I$_o$) |
|---|---|
| 13.3 | 18 |
| 9.41 | 100 |
| 6.62 | 6 |
| 5.93 | 41 |
| 5.41 | 48 |
| 5.03 | 2 |
| 4.69 | 6 |
| 4.41 | 50 |
| 4.19 | 34 |
| 3.93 | 22 |
| 3.81 | 18 |
| 3.66 | 6 |
| 3.41 | 13 |
| 3.21 | 35 |
| 3.02 | 28 |
| 2.94 | 21 |
| 2.81 | 26 |
| 2.75 | 9 |
| 2.64 | 11 |
| 2.59 | 2 |
| 2.54 | 9 |

The preparation of zeolite L described in Inorganic Chemistry, Vol. 5, No. 9, September 1966, pages 1539-1541 comprises cyrstallizing the zeolite from a reaction mixture comprising mole ratios:

| Na$_2$O/Al$_2$O$_3$ + RO/Al$_2$O$_3$ | 6-19 |
|---|---|
| Na$_2$O/Al$_2$O$_3$ | 1.5-2.3 |
| SiO$_2$/Al$_2$O$_3$ | 4-11 |
| H$_2$O/Al$_2$O$_3$ | 200-700 |

U.S. Pat. No. 4,001,106 describes a preparation from an aqueous solution of oxides having a composition in terms of mole ratio of oxides as follows:

| SiO$_2$/Al$_2$O$_3$ | 2.5-15 |
|---|---|
| Na$_2$O/(Na$_2$O + RO) | 0.01-0.25 |
| H$_2$O/(Na$_2$O + RO) | 25-50 |
| (Na$_2$ + RO)/SiO$_2$ | 1-2 | at a temperature of 90° C.-120° C.

"Synthesis and Nature of some salt-bearing Aluminosilicates" Barrer and Marcilly, J. C. S., Section A, pages 2735-2745 (1970) describes an alternative preparation via intermediate phases designated P (Cl), P'(Cl), Q(Br) and Q'(Br), which are in turn prepared by reaction of a barium halide upon a potassium or barium aluminosilicate gel, or on zeolite X, Y, analcite or chabazite.

U.S. Pat. No. 4,496,528 describes a variation of this process in which zeolite P(Cl), P'(Cl), Q(Br) or Q'(Br) are extracted to remove barium ions. The product prepared in this way is of the formula:

$$0.5-0.9 \; M_2O/0.2-0.5 \; BaO/Al_2O_3/2.5-7 \; SiO_2 0-0.3 \; BaCl_2/0-7 \; H_2O$$

and has the following X-ray diffraction pattern:

| d(A) | I/I$_o$ |
|---|---|
| 13.26 | 50 |
| 9.34 | 100 |
| 7.65 | 12 |
| 6.60 | 15 |
| 5.92 | 22 |
| 5.40 | 34 |
| 5.01 | 15 |
| 4.67 | 9 |
| 4.42 | 56 |
| 4.19 | 50 |
| 3.99 | 26 |
| 3.83 | 40 |
| 3.67 | 15 |
| 3.42 | 19 |
| 3.30 | 9 |
| 3.21 | 44 |
| 3.12 | 11 |
| 3.05 | 74 |
| 2.96 | 23 |
| 2.89 | 9 |
| 2.83 | 53 |
| 2.77 | 19 |
| 2.71 | 11 |
| 2.65 | 22 |
| 2.60 | 7 |
| 2.55 | 22 |

SU 1155564 discloses preparation of a (Na, Li) ZK-5 of the formula:

$$0.11-0.20Li_2O: 0.89-0.80Na_2O: Al_2O_3: 3.08-3.28SiO_2: 5-5.3H_2O$$

from a reaction mixture comprising the following mole ratios:

$$(Li_2O+Na_2O)/SiO_2=0.9-1.2$$

$$Na_2O/(Na_2O+Li_2O)=0.45-0.7$$

$$H_2O/(Na_2O+Li_2O)=60-75$$

$$SiO_2/Al_2O_3=5$$

U.S. Pat. No. 3,720,753 describes a zeolite similar to ZK-5 having stoichiometric mole ratios of oxides, as follows:

$$0.1-0.4Cs_2O:0.6-0.9M_2O:Al_2O_3:YSiO_2:ZH_2O$$

wherein M may be either potassium or a mixture of potassium and sodium such that the ratio Na/K$\leq$1, and Z may be any value from 0 to about 10, and wherein Y is from 4 to about 7, preferably from 6 to about 7, and most preferably from greater than 6 to about 7.

The X-ray diffraction pattern of this zeolite is:

| d | I/I° |
|---|---|
| 13.39 | 47 |
| 9.46 | 68 |
| 7.73 | 15 |
| 6.68 | 30 |
| 5.95 | 100 |
| 5.44 | 2 |
| 5.04 | 6 |
| 4.43 | 43 |
| 4.21 | 47 |
| 3.84 | 51 |
| 3.69 | 9 |
| 3.43 | 53 |
| 3.22 | 60 |
| 3.13 | 9 |
| 3.04 | 26 |
| 2.96 | 32 |
| 2.89 | 4 |
| 2.83 | 53 |
| 2.65 | 15 |
| 2.55 | 34 |

This synthetic zeolite, having pores within the range of 3 to 5.5 Å units, and in its purest form from 3 to 4 Å units, is prepared from an aqueous reaction mixture containing silica, alumina, and either a mixture of potassium oxide and cesium oxide, or potassium oxide, cesium oxide and a small amount, i.e. preferably less than about 3 percent, of sodium oxide. The proportions of these reactants in the initial reaction mixture are determined from the following molar ratios:

| | Reactant Molar Ratios | | |
|---|---|---|---|
| | Broad | Preferred | Particularly Preferred |
| $SiO_2/Al_2O_3$ | 3–12 | 5–10 | 7–9 |
| $K_2O + Cs_2O/SiO_2$ | 0.20–0.40 | 0.25–0.32 | about 0.30 |
| $Cs_2O/K_2O + Cs_2O$ | 0.05–0.35 | 0.10–0.30 | 0.15–0.25 |
| $Na_2O/K_2O + Cs_2O$ | 0–0.5 | 0–0.4 | 0–0.2 |
| $H_2O/SiO_2$ | 5–12 | 7–10 | 8–9 |

It has now been found that a new form of zeolite ZK-5, capable of being more siliceous than the prior art forms, and containing strontium may be prepared directly from a reaction mixture containing strontium.

Thus, in one aspect the invention provides a zeolite having the formula:

0.9–1.3[(1−x)$M_{2/n}O$+xSrO]: $Al_2O_3$: 4–10 $SiO_2$: 0–10 $H_2O$ (wherein M is a cation of valence n and x is from greater than 0 to 0.3) and having an X-ray diffraction pattern (CuK α) having the following characteristic d(Å) values:

TABLE A

| |
|---|
| 9.3 ± 0.1 |
| 5.40 ± 0.03 |
| 4.41 ± 0.03 |
| 4.18 ± 0.03 |
| 3.98 ± 0.02 |
| 3.82 ± 0.02 |
| 3.21 ± 0.02 |
| 3.03 ± 0.02 |
| 2.95 ± 0.01 |

TABLE A-continued

| |
|---|
| 2.82 ± 0.01 | and preferably having the following more prominent d(Å) values:

TABLE B

| |
|---|
| 13.1 ± 0.2 |
| 9.3 ± 0.1 |
| 6.60 ± 0.04 |
| 5.91 ± 0.04 |
| 5.40 ± 0.03 |
| 4.41 ± 0.03 |
| 4.18 ± 0.03 |
| 3.98 ± 0.02 |
| 3.82 ± 0.02 |
| 3.66 ± 0.02 |
| 3.21 ± 0.02 |
| 3.03 ± 0.02 |
| 2.95 ± 0.01 |
| 2.82 ± 0.01 |
| 2.64 ± 0.01 |
| 2.54 ± 0.01 |

In a preferred aspect the zeolite is of the formula:

0.7–1.1 $M'_{2/n}O$: 0.001–0.3 SrO: $Al_2O_3$: 6–10 $SiO_2$: 0–10 $H_2O$ wherein M' is an alkaline earth or alkali metal of valence n.

The zeolite of the invention has the structure of zeolite ZK-5 but differs in that higher silica/alumina ratios may be prepared than have previously been reported. Thus in a further aspect this invention provides zeolite ZK-5 having a silica/alumina ratio of greater than 7, preferably from 7.5 to 10.

The zeolites also differ from reported forms of zeolite ZK-5 in containing strontium. It has been noted that the intensity of some of the characteristic lines of ZK-5 differ from those previously quoted for ZK-5, and this is believed at least in part to be a result of the presence of strontium. In another aspect this invention provides a zeolite ZK-5 containing strontium, whether introduced by synthesis, impregnation or ion exchange but preferably where the strontium is introduced by synthesis.

In a particularly preferred aspect of the invention the cation M or M' is or includes the potassium ion. Thus, in another aspect the invention provides zeolite ZK-5 in the potassium form—that is, of the formula:

0.7–1.1 $K_2O$: 0.001–0.3 SrO: $Al_2O_3$: 6–10 $SiO_2$: 0–10 $H_2O$

Notwithstanding the preference for the potassium form of ZK-5, it may be desirable to include small amounts of other ions in addition to the preferred potassium in the synthesis of ZK-5 such as other alkali metals, alkaline earth metals. In addition, the synthesized potassium form of ZK-5 may be impregnated or exchanged with other ions to remove or replace at least a part of the potassium therein.

The zeolite of the invention displays an X-ray diffraction pattern typical for zeolite ZK-5, subject to the changes in position and intensity of the X-ray as may be expected to result from ion exchange, or different ratios of elements within the zeolite. Additional lines not belong to the pattern for zeolite ZK-5 may appear in a pattern. This is an indication that one or more additional crystalline materials are mixed with zeolite ZK-5 in the sample beg tested. It is a preferred feature of the invention that the amount of such additional crystalline materials is minimised in the zeolite material as synthesized. In particular, it is preferred that the synthesis of the zeolite of the invention is conducted so that the amount of zeolite W or zeolite L in the product of the synthesis is minimised.

The zeolites of the invention are preferably aluminosilicates and will be described hereinafter in terms of aluminosilicates, though other elemental substitutions are possible, for example aluminium may be substituted by gallium, boron, iron and similar trivalent elements, and silicon may be substituted by elements such as germanium or phosphorus.

The zeolites of the invention may be hydrated, typically with up to 10 moles of water per mole of $Al_2O_3$. When used as a catalyst base, as described hereinafter, the zeolite of the invention is preferably first calcined to remove water. In normal preparation from aqueous gels a hydrated form is first prepared and this may be dehydrated by heating.

The invention also provides a process for the preparation of zeolite ZK-5, in which an alkaline reaction mixture comprising water, a source of a metal M, a source of silicon, a source of aluminium and a source of strontium, with a composition falling within the following molar ratios (expressed as oxides):

| | |
|---|---|
| $(M_2O + SrO)/SiO_2$ | 0.16–0.30 |
| $H_2O/(M_2O + SrO)$ | 25–120 |
| $SiO_2/Al_2O_3$ | 8–12 |
| $SrO/SiO_2$ | 0.001–0.03 |

(wherein M is as defined hereinbefore, preferably potassium) is heated to a temperature of from at least 75° C. and preferably from 100° C. to 250° C., more preferably from 120° C. to 225° C.

The principal components to the reaction mixture or synthesis gel are thus generally:

| |
|---|
| aluminium |
| silicon |
| alkali metal, preferably potassium |
| strontium |
| water | and optionally one or more additional metals as described hereinbefore and the relative proportions of these components and the chosen reaction conditions are important if the desired zeolite of the invention is to be obtained.

Thus, the zeolites of the invention are preferably obtained within the following preferred ranges:

| | |
|---|---|
| $(K_2O + SrO)/SiO_2$ | 0.17–0.25 |
| $H_2O/(K_2O + SrO)$ | 50–120 |
| $SiO_2/Al_2O_3$ | 8–12 |
| $SRO/SiO_2$ | 0.002–0.025 |

In addition to varying the proportions of the reactants in the reaction mixture, it is possible to vary the reaction conditions and in particular the crystallisation temperature. By using different temperatures, it may be possible to deviate further from the desired product. In general, within the broad reactant ratios defined for the process of the invention, a higher crystallisation temperature enables the silicon content to be lowered and/or the water content to be lowered and/or the potassium content (and thus the alkalinity) to be raised.

In the synthesis of the zeolite of the invention, the source of silicon for the reaction mixture is generally silica, and this is usually most conveniently in the form of a colloidal suspension of silica such as Ludox HS 40 available from E. I. Dupont de Nemours and Co. Colloidal silica sols are preferred since they result in less contaminating phases. However, other forms such as silicates may be used.

The source of aluminium may be an alumina introduced into the reaction medium as, for example, $Al_2O_3.3H_2O$, previously dissolved in alkali. However, it is also possible to introduce aluminium in the form of the metal, which is dissolved in alkali.

The zeolites of the invention are preferably obtained from reaction mixtures containing potassium. This potassium is preferably introduced as potassium hydroxide.

The source of strontium is preferably strontium hydroxide though other convenient strontium compounds such as the nitrate, carbonate, oxide or sulphate may be used.

The product of the processes described above is a mixed cation form of the zeolite containing alkali metal, preferably potassium, and strontium. By ion exchange of the product in the manner conventional to zeolite chemistry, other cations can be introduced.

It is also possible to add small amounts of other bivalent metal cations to the synthesis gel, such as barium, magnesium and other alkaline earth metals, copper, manganese, chromium, lead, iron, cobalt, nickel and zinc. These cations present in amounts as small as 1 to 1000 ppms may have effect in promoting formation of zeolite ZK-5.

Crystallisation time is related to the crystallisation temperature. The crystallisation is preferably carried out in the region of 150° C. and at this temperature the crystallisation time may be from 24 to 160 hours, typically from 72 to 130 hours. Lower temperatures may require much longer times to achieve good yield of the desired product.

The crystallisation is generally carried out in a sealed autoclave and thus at autogenous pressure. Lower pressure will require longer crystallisation times.

Following the preparation as described above the zeolite ZK-5 may be separated, washed and dried in the normal manner.

The ability of the above process to produce zeolite ZK-5 is surprising since in the absence of strontium, the preparation would be expected to form zeolite L, as described in EP-A-96479, or zeolite W or a mixture depending upon the alkalinity of the synthesis gel.

The products of the processes of the invention described herein before are preferably substantially free from contaminant crystalline and amorphous materials. However, in employing these products in catalytic applications it may be desired to combine them with additional crystalline or amorphous materials as binders and this invention extends to such combinations. Thus, the invention extends to catalysts comprising a zeolite of the invention and a binder.

Zeolite ZK-5 is known to be useful as a cracking catalyst, for example in selective hydrocracking of linear paraffins or in reforming, and the zeolites of the invention may also be used in such applications, where the higher silica/alumina ratios obtainable in the invention may be advantageous. Other suitable applications are recovery of linear paraffins, clean-up of organic compounds such as linear paraffins or xylenes by selective removal of contaminants, and separation of propene from propane.

The catalysts of the present invention are also suitable for use in fluid catalytic cracking wherein a relatively heavy petroleum feedstock (BP 218°–566° C.) is converted to lower boiling products, usually in the heating oil or gasoline (or lighter) range. Typical fluid catalytic cracking conditions include a temperature range of from 466° to 510° C., with oil feed temperatures from 316° to 454° C., and regenerator exit temperatures for catalyst from 593° to 677° C.

The following Examples are now given though only by way of illustration to show certain aspects of the invention in more detail.

EXAMPLE 1

Preparation of Zeolite ZK-5 using Strontium

A synthesis gel was prepared from potassium hydroxide pellets (87.3%), aluminium hydroxide powder, strontium hydroxide octahydrate, Ludox HS-40 (a silica colloid) and demineralised water to give a molar composition of:

2.31 $K_2O$/0.1 $SrO/Al_2O_3$/10 $SiO_2$/160 $H_2O$

In the absence of strontium this gel would crystallize to form zeolite L. Instead the gel was crystallized for 91 hours at 500° C. in a 300 ml stainless steel autoclave, washed and dried and examined by XRD. The product was highly crystalline and had XRD-pattern of zeolite ZK-5. The X-ray data is given below:

TABLE C

| d(Å) | Relative Intensity |
|---|---|
| 13.14 | 22 |
| 9.32 | 100 |
| 6.60 | 26 |
| 5.89 | 24 |
| 5.39 | 35 |
| 5.00 | 18 |
| 4.67 | 7 |
| 4.40 | 102 |
| 4.17 | 86 |
| 3.98 | 34 |
| 3.21 | 47 |
| 3.66 | 25 |
| 3.41 | 16 |
| 3.20 | 53 |
| 3.03 | 87 |
| 2.95 | 36 |
| 2.82 | 80 |
| 2.75 | 12 |
| 2.64 | 37 |
| 2.59 | 10 |
| 2.54 | 39 |

TABLE C-continued

| d(Å) | Relative Intensity |
|---|---|
| Unit cell dimension a = 18.68 Å | |

EXAMPLES 2 AND 3

Comparative Examples A and B

The synthesis of Example 1 was repeated with various amounts of Sr in the synthesis gel. In these syntheses the Sr content was varied from 0.45 to 0.006 wt %. The gel compositions tested were in the range:

2.30 $K_2O$/(0.2–0.0025) $SrO/Al_2O_3$/10 $SiO_2$/160 $H_2O$ save that in Comparative Example B the amount of $K_2O$ was increased to 2.50 in the above expression.

The gels were aged in 300 ml stainless steel autoclaves for 69 hours at 150° C. to bring about crystallization.

After washing and drying the products were examined by X-ray diffraction. The products identified in the X-ray patterns are given below:

| Example | Sr content in gel molar ratio wt % | | Zeolite product obtained |
|---|---|---|---|
| | $SrO/SiO_2$ | Sr | XRD |
| 2 | 0.02 | 0.45 | ZK-5 |
| 3 | 0.0025 | 0.05 | ZK-5 |
| A | 0.0005 | 0.01 | L + ZK-5 |
| B | 0.00025 | 0.006 | L |

These results show that in this type of synthesis gel as little as 0.05 wt % of Sr species is sufficient to obtain pure zeolite ZK-5 according to the invention, while at lower amounts zeolite L is formed.

EXAMPLES 4–9

Synthesis using low alkalinity synthesis gels

To investigate a possible further increase in the $SiO_2/Al_2O_3$ ratio in the product the procedure of Example 1 was repeated with low alkalinity synthesis mixtures. Some of these synthesis gels were also seeded with traces of Ba; this was done to investigate whether it is possible to increase the formation rate of ZK-5, since this effect has been observed in the synthesis of zeolite L. In these syntheses the product yield was accurately measured because an increase in product yield will indicate an increased siliceousness of the product. The results are given below:

| Example | Synthesis Gel Alkalinity $K_2O/SiO_2$ molar ratio | Product Characteristics XRD | | | Yield %[a] |
|---|---|---|---|---|---|
| | | phase | % cryst. | $SiO_2/Al_2O_3$ | |
| 4 | 0.23[b] | ZK-5 | 100[c] | 7.1 | 17.4 |
| 5 | 0.20[b] | ZK-5 | 129 | | 18.6 |
| 6 | 0.18[b] | ZK-5 | 93 | 8.4 | 19.4 |
| 7 | 0.18 | ZK-5 | 74 | | 19.8 |
| 8 | 0.16 | ZK-5[d] | n.a.[e] | | n.a. |
| 9 | 0.26 | ZK-5[d] | n.a. | | n.a. |

[a]product yield: wt ratio dry product/gel × 100.
[b]gels were seeded with Ba(BaO/10 $SiO_2$ ratio 0.005).
[c]arbitrarily set at 100%.
[d]some contaminant present.
[e]not available.

These experiments show that ZK-5 can crystallize from extremely low alkaline synthesis mixtures, and that traces of Ba seems to enhance the formation of ZK-5. Reducing the gel alkalinity tends to increase the product yield and the $SiO_2/Al_2O_3$ ratio.

Certain of the zeolite ZK-5 products of the invention were analysed for elemental composition. The results are given below:

| Example | Product Composition | | Sr content wt % |
|---|---|---|---|
| | K/Al molar ratios | $SiO_2/Al_2O_3$ molar ratios | |
| 2 | 1.05 | 7.1 | 2.26 |
| 3 | 0.95 | 6.7 | 0.25 |
| 6 | 1.07 | 8.4 | 1.05 |

The product of Example 2 was tested and its n-hexane adsorption was measured at 11.6% at $p/Po=0.5$, $T=30°$ C.

What is claimed is:

1. A method of preparing zeolite ZK-5 by synthesis from a reaction mixture containing strontium, said method comprising:
   (a) providing an alkaline reaction mixture comprising water, a source of a metal M, a source of silicon, a source of aluminium, and a source of strontium, said reaction mixture having a composition defined by the following molar ratios (expressed as oxides):

| | |
|---|---|
| $(M_{2/n}O + SrO)/SiO_2$ | 0.16–0.30 |
| $H_2O/(M_{2/n}O + SrO)$ | 25–120 |
| $SiO_2/Al_2O_3$ | 8–12 |
| $SrO/SiO_2$ | 0.001–0.03 | wherein M is a cation of valence n;
   (b) heating said reaction mixture to a temperature of from at least 75° C.; and
   (c) recovering said zeolite ZK-5.

2. The method of claim 1, wherein said reaction mixture is heated to a temperature of from about 120° C. to about 225° C.

3. The method of claim 2, wherein said reaction mixture has a composition defined by the following molar ratios:

| | |
|---|---|
| $(K_2O + SrO)/SiO_2$ | 0.17–0.25 |
| $H_2O/(K_2O + /SrO)$ | 50–120 |
| $SiO_2/Al_2O_3$ | 8–12 |
| $SrO/SiO_2$ | 0.002–0.025. |

4. The method of claim 1, wherein said reaction mixture further comprises from about 1 to about 1,000 ppm of at least one bivalent metal cation selected from the group consisting of barium, magnesium, manganese, chromium, copper, lead, iron, cobalt, nickel, zinc, and mixtures of barium, magnesium, manganese, chromium, copper, lead, iron, cobalt, nickel and zinc.

* * * * *